United States Patent [19]
Saito et al.

[11] Patent Number: 5,621,145
[45] Date of Patent: Apr. 15, 1997

[54] BISAMIDOXIME COMPOUND, PROCESS FOR PREPARING THE SAME AND A FLUORINE-CONTAINING ELASTOMER COMPOSITION COMPRISING THE SAME

[75] Inventors: Satoru Saito; Haruyoshi Tatsu, both of Ibaraki, Japan; Lev Solomonovich, deceased, late of Moscow, Russian Federation, by Elena N. German, heiress; Ziefman Y. Vilovich, Moscow, Russian Federation; Postovoi S. Anatol'evich, Moscow region, Russian Federation; Sterlin S. Rafailovich, Moscow, Russian Federation

[73] Assignee: Nippon Mektron, Limited, Tokyo, Japan

[21] Appl. No.: 583,469

[22] Filed: Jan. 5, 1996

[30] Foreign Application Priority Data

Feb. 16, 1995 [JP] Japan .................... 7-051977

[51] Int. Cl.⁶ ................................. C07C 259/18
[52] U.S. Cl. .................. 564/229; 558/389; 558/419; 558/420; 558/426; 558/448; 558/449; 564/226; 528/362; 528/401; 528/402
[58] Field of Search ................... 564/226, 229; 528/362, 401, 402; 558/389, 419, 420, 426, 448, 449

[56] References Cited

U.S. PATENT DOCUMENTS

| | | | |
|---|---|---|---|
| 4,145,524 | 3/1979 | Frosch et al. | 528/401 |
| 4,273,918 | 6/1981 | Rosser et al. | 528/310 |
| 4,443,629 | 4/1984 | Bonse et al. | 564/226 |

FOREIGN PATENT DOCUMENTS

| | | |
|---|---|---|
| 0601977A1 | 6/1994 | European Pat. Off. . |
| 59-109546 | 11/1983 | Japan . |

*Primary Examiner*—Peter O'Sullivan
*Attorney, Agent, or Firm*—Barnes & Thornburg

[57] ABSTRACT

When a novel bisamidoxime compound represented by the following general formula:

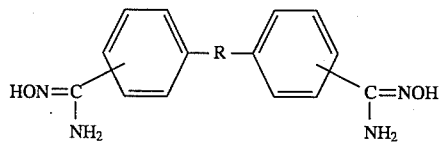

where R is an alkylidene group having 1 to 6 carbon atoms, or a perfluoroalkylidene group having 1 to 10 carbon atoms, is used as a vulcanizing agent for fluorine-containing elastomers having cyano groups as cross-linkable groups, the resulting vulcanizates having a satisfactory compression set are obtained without any problem of processability such as roll kneadability, etc.

8 Claims, No Drawings

BISAMIDOXIME COMPOUND, PROCESS FOR PREPARING THE SAME AND A FLUORINE-CONTAINING ELASTOMER COMPOSITION COMPRISING THE SAME

BACKGROUND OF THE INVENTION

1. Field of the Invention

The present invention relates to a bisamidoxime compound, a process for preparing the same and a fluorine-containing elastomer composition comprising the same, and more particularly a novel bisamidoxime compound, a process for preparing the same and a fluorine-containing elastomer composition comprising a fluorine-containing elastomer having cyano group as cross-linkable groups and the bisamidoxime compound as a vulcanizing agent.

2. Related Art

JP-A-59-109546 discloses a fluorine-containing elastomer composition comprising a terpolymer of tetrafluoroethyleneperfluoro(methyl vinyl ether)-perfluoro unsaturated nitrile compound represented by the following general formula:

$$CF_2=CF[OCF_2CF(CF_3)]nO(CF_2)mCN$$

where n is an integer of 1 to 2 and m is an integer of 1 to 4, and a bis(aminophenyl) compound represented by the following general formula:

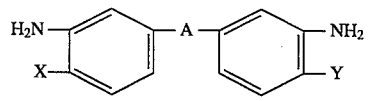

wherein A is an aikylidene group having 1 to 6 carbon atoms, a perfluoroalkylidene group having 1 to 10 carbon atoms, $SO_2$, O, CO or a carbon-carbon bond of directly bonding two benzene rings, and X and Y are hydroxyl groups or amino groups, as a curing agent. However, the vulcanization products resulting from vulcanization of such a fluorine-containing elastomer composition have no satisfactory compression set.

The present inventors proposed a bisamidrazone compound represented by the following general formula:

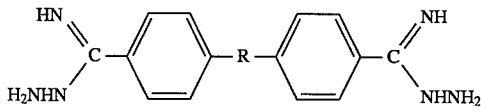

as a novel vulcanizing agent capable of giving a vulcanization product having a satisfactory compression set when used as a vulcanizing agent for the fluorine-containing elastomer having cyano groups as cross-linkable groups (Japanese Patent Application No. 282943/1994). The proposed bisamidrazone compound can give a vulcanization product having a satisfactory compression set when used as a vulcanizing agent for the fluorine-containing elastomer having cyano groups as cross-linkable groups, but has a higher reactivity to the cyano groups as cross-linkable groups and sometimes generates scorching, depending on kneading temperature, shearing force, etc. when the composition is kneaded by two roll mills, etc. prior to the vulcanization.

SUMMARY OF THE INVENTION

An object of the present invention is to provide a novel vulcanizing agent compound capable of giving a vulcanizate having a satisfactory compression set without any problems of processing such as roll kneadability, etc. when a fluorine-containing elastomer having cyano groups as cross-linkable groups is kneaded and vulcanized.

According to the present invention, a novel bisamidoxime compound represented by the following general formula:

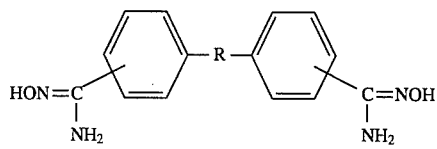

where R is an alkylidene compound having 1 to 6 carbon atoms, or a perfluoroalkylidene compound having 1 to 10 carbon atoms, is provided and can serve as a suitable vulcanization agent for fluorine-containing elastomers having cyano group as crosslinkable groups.

DETAILED DESCRIPTION OF THE INVENTION

The present bisamidoxime compound can be readily prepared by reaction of a bis(cyanophenyl) compoound represented by the following general formula:

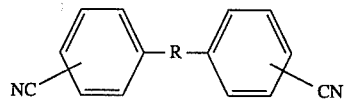

with a hydroxylamine or its salt.

In the bis(cyanophenyl) compoound represented by the foregoing general formula, R is preferably an alkylidene group such as an isopropylidene group or a perfluoroalkylidene group such as a perfluoroisopropylidene group, and compounds represented by the following general formula are preferably used:

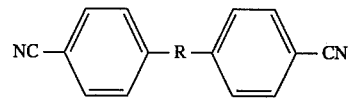

Reaction of the bis(cyanophenyl) compound with the hydroxylamine or its salt such as hydrochloride, sulfate etc. can be readily carried out in a solvent such as methanol, ethanol or the like generally at the reflux temperature, using the hydroxylamine or its salt in a molar amount by at least twice more than that of the bis(cyanophenyl) compound and an aqueous solution of a basic substance such as sodium hydroxide, potassium hydroxide or the like as a catalyst.

The thus obtained bisamidoxime compound is used as a vulcanizing agent for a fluorine-containing elastomer having cyano groups as cross-linkable groups. The fluorine-containing elastomer for use in the present invention includes, for example, a terpolymer consisting of 45 to 75% by mole of tetrafluoroethylene, 54.8 to 20% by mole of perfluoro(lower alkyl vinyl ether) and 0.2 to 5% by mole of perfluoro unsaturated nitrile compound.

As the perfluoro(lower alkyl vinyl ether), perfluoro (methyl vinyl ether) is usually used.

As the perfluoro unsaturated nitrile compound serving as a cross-linking site monomer, the following compounds are used:

$$CF_2=CFO(CF_2)nOCF(CF_3)CN \qquad \text{(n: 2–5)}$$

-continued

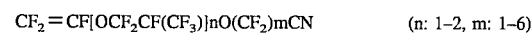 (n: 1–2, m: 1–6)

 (n: 2–12)

 (n: 1–2)

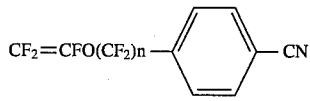 (n: 1–6)

The terpolymer consisting of the foregoing components as essential ones can be further copolymerized with such an amount of fluorinated olefines or various vinyl compounds as not to inhibit the copolymerization reaction or deteriorate the physical properties of vulcanization products, for example, not more than 20% by mole. The fluorinated olefine includes, for example, vinylidene fluoride, monofluoroethylene, trifluoroethylene, trifluoropropylene, pentafluoropropylene, hexafluroprophylene, hexafluoroisobutylene, chlorotrifluoroethylene, dichlorodifluoroethylene, etc. The vinyl compound includes, for example, ethylene, prophylene, 1-butene, isobutylene, methyl vinyl ether, ethyl vinyl ether, butyl vinyl ether, cyclohexyl vinyl ether, vinyl acetate, vinyl propionate, vinyl chloride, vinylidene chloride, trifluorostyrene, etc.

In the present invention, about 0.2 to about 5 parts by weight, preferably about 0.5 to about 2 parts by weight, of the bisamidoxime compound represented by the foregoing general formula is used as a cross-linking agent per 100 parts by weight of the terpolymer.

The present fluorine-containing elastomer composition comprising the foregoing components as essential ones can further contain an inorganic filler such as carbon black, silica, etc., an acid receptor such as divalent metal oxide or hydroxide, stearic acid salt, litharge, etc. and other necessary additives, when required. The present composition can be prepared by kneading in two roll mills, a kneader, Bambury mixer or the like, and the cross-linking is carried out by heating the composition at a temperature of about 100 to about 250° C. for about 1 to about 120 minutes. Post cure is carried out preferably in an inert atmosphere such as a nitrogen gas atmosphere, at a temperature of about 150 to about 320° C. within about 30 hours.

As described above, the present invention provides a novel bisamidoxime compound. When the present bisamidoxime compound is used as a vulcanizing agent for fluorine-containing elastomers having cyano groups as cross-linking groups, vulcanizates having a satisfactory compression set can be obtained without any problems of processing such as roll kneadability, etc.

PREFERRED EMBODIMENTS OF THE INVENTION

The present invention will be described in detail below, referring to Examples.

EXAMPLE 1

A solution containing 13.4 g of 2,2-bis(4-cyanophenyl)hexafluoropropane and 8.0 g of hydroxylamine.hydrochloride in 100 ml of ethanol was added to 100 ml of an aqueous solution containing 4.5 g of sodium hydroxide, and the resulting mixture was refluxed for 14 hours. Then, the reaction mixture was poured into 500 ml of water to precipitate the product. The precipitates were recovered therefrom by filtration, washed with water and dried under reduced pressure in an anhydrous $P_2O_5$-containing desiccator, whereby 15 g of crude product was obtained (yield: 92%). Then, the crude product was recrystallized from 5% water-containing acetone, whereby 2,2-bis(4-carboxyphenyl)hexafluoropropane bisamidoxime of the following chemical formula was obtained as white crystals.

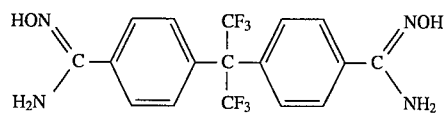

Melting point: 217–219° C. (decomposed)

Elemental analysis ($C_{17}TH_{14}F_6N_4O_2$): Calculated; C 48.57%, H 3.33%, F 27.14% Found; C 48.65%, H 3.23%, F 26.48%

Mass spectrum (m/z): 420($M^+$)

REFERENCE EXAMPLE 1

51 kg of distilled water, 900 g of ammonium perfluorooctanoate and 782 g of potassium dihydrogen phosphate were charged into a stainless steel autoclave having a net capacity of 100 liters, and then the inside gas in the autoclave was replaced with a nitrogen gas. Then, the autoclave was subjected to pressure reduction, and the following compounds were successively charged into the autoclave:

| | |
|---|---|
| Tetrafluoroethylene [TFE] | 1.57 kg |
| Perfluoro(methyl vinyl ether) [FMVE] | 1.90 kg |
| Perfluoro(5-cyanopentyl vinyl ether) [CPVE] | 90 g |

Then, the autoclave was heated to 60° C., and 5 liters of an aqueous solution containing 150 g of ammonium persulfate and 26 g of sodium sulfite was added thereto to initiate polymerization reaction.

During the polymerization reaction, TFE, FMVE and CPVE were additionally supplied to the autoclave at feed rates of 1.2 kg/hr, 1.4 kg/hr and 75 g/hr, respectively, to maintain the inside pressure of the autoclave at 8.0–9.0 $kg/cm^2$ gage. 7 hours after the start of polymerization reaction, the additional supply was discontinued and the autoclave was kept in that state for one hour. Then, the autoclave was cooled and the residual gas was purged therefrom, whereby 78 kg of aqueous latex containing 27% by weight of solid matters was obtained.

Then, the thus obtained aqueous latex was added to a mixture consisting of 80 liters of an aqueous 5 wt. % magnesium chloride solution and 80 liters of ethanol to coagulate the latex. Then, the aggregate was washed with water and dried at 80° C. under the atmospheric pressure for 70 hours, whereby 19.8 kg of white rubbery terpolymer A was obtained (yield: 88%).

It was found by ultraviolet spectrum and NMR analysis that the thus obtained rubbery terpolymer had the following composition.

TFE 68.8 mol. %

FMVE 30.0 mol. %

CPVE 1.2 mol. %

REFERENCE EXAMPLE 2

55 kg of distilled water, 1,800 g of ammonium perfluorooctanoate and 782 g of potassium dihydrogen phosphate were charged into a stainless steel autoclave having a net capacity of 100 liters, and then the inside gas in the autoclave was replaced with a nitrogen gas. Then, the autoclave was subjected to pressure reduction. Then, the following compounds were successively charged into the autoclave:

Tetrafluoroethylene [TFE] 1.26 kg

Perfluoro (methyl vinyl ether) [FMVE] 1.30 kg

Perfluoro (2-cyano-3,7-dioxa-8-nonene) [CEPVE] 170 g

Then, the autoclave was heated to 60° C., and 5 liters of an aqueous solution containing 200 g of ammonium persulfate and 36 g of sodium sulfite was added thereto to initiate polymerization reaction.

During the polymerization reaction, TFE, FMVE and CEPVE were additionally supplied to the autoclave at feed rates of 2.09 kg/hr, 2.25 kg/hr and 267 g/hr, respectively, to maintain the inside pressure of the autoclave at 8.0–9.0 kg/cm$^2$ gage. 4.5 hours after the start of polymerization reaction, the additional supply was discontinued and the autoclave was kept in that state for one hour. Then, the autocalve was cooled and the residual gas was purged therefrom, whereby 78 kg of aqueous latex containing 28% by weight of solid matters was obtained.

Then, the thus obtained aqueous latex was added to a mixture consisting of 80 liters of an aqueous 5 wt. % magnesium chloride solution and 80 liters of ethanol to coagulate the latex. Then, the aggregate was washed with water and dried at 80° C. under the atmospheric pressure for 70 hours, whereby 20.9 kg of white rubbery terpolymer B was obtained (yield: 89%).

It was found by infrared spectrum and NMR analysis that the rubbery terpolymer ($\eta$sp/c: 0.59 dl/g) had the following composition.

TFE 72.1 mol. %

FMVE 25.5 mol. %

CEPVE 2.4 mol. %

EXAMPLE 2

100 parts by weight of the rubbery terpolymer A or B obtained in Reference Example 1 or 2, respectively, was admixed with 20 parts by weight of MT carbon black and 0.5 parts by weight of 2,2-bis(4-carboxyphenyl)hexafluoropropane bisamidoxime, and the mixture was kneaded in two roll mills. Then, the kneaded mixture was press-vulcanized at 180° C. for 30 minutes and then oven-vulcanized in a nitrogen atmosphere successively stagewise under the following conditions:

1st stage: Keeping at 90° C. for 4 hours,

2nd stage: Heating to 204° C. over 6 hours,

3rd stage: Keeping at 204° C. for 18 hours,

4th stage: Heating to 288° C. over 6 hours, and

5th stage: Keeping at 288° C. for 18 hours.

COMPARATIVE EXAMPLE

In Example 2, the same amount of 2,2-bis(4-carboxyphenyl)hexafluoropropane bisamidrazone of the following chemical formula was used in place of 2,2-bis(4-carboxyphenyl)hexafluoropropane bisamidoxime.

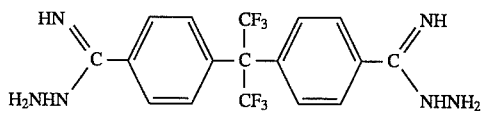

The vulcanization products obtained in Example 2 and Comparative Example were subjected to determination of the following measurement items:

Normal state physical properties:

Hardness according to DIN 53505

Tensile test according to DIN 53504 for 100% modulus, tensile strength and elongation Heat ageing test: Normal state physical properties after ageing in air at 300° C. for 70 hours.

Compression set: ASTM Method B/P-24 O-ring

Hot water resistance: Percent volume swelling after immersion in pressurized water at 200° C. for 70 hours.

Vulcanized sheet surface: Visual determination of the presence of surface unevenness Results of determination are shown in the following Table.

TABLE

| Measurement items | | Example 2 Terpolymer A | B | Comp. Ex. Terpolymer A | B |
|---|---|---|---|---|---|
| [Normal state physical properties] | | | | | |
| Hardness | | 73 | 72 | 75 | 72 |
| 100% modulus | (MPa) | 8.0 | 7.6 | 9.3 | 9.0 |
| Tensile strength | (MPa) | 21.1 | 17.2 | 21.6 | 21.2 |
| Elongation | (%) | 170 | 160 | 160 | 170 |
| [Heat ageing test] | | | | | |
| Hardness | | 72 | 71 | 74 | 72 |
| 100% modulus | (MPa) | 5.6 | 6.1 | 8.0 | 6.9 |
| Tensile strength | (MPa) | 20.9 | 15.0 | 21.4 | 18.4 |
| Elongation | (%) | 211 | 170 | 190 | 211 |
| [Compression set] | | | | | |
| 300° C. for 70 hours | (%) | 35 | 30 | 32 | 36 |
| [Hot water resistance] | | | | | |
| Percent volume swelling | (%) | 4.6 | 1.4 | 3.6 | 1.9 |
| [Vulcanized sheet surface] | | | | | |
| Presence of surface unevennesst | | none | none | none | existed |

When a bisamidrazone compound is used as a vulcanizing agent, vulcanization reaction sometimes proceeds partially during the roll kneading. The resulting composition has a poor roll kneadability, sometimes resulting in fluctuations in the physical properties of the final vulcanizates. In the press molding, poor flowing, rough vulcanization molding product surfaces after the secondary vulcanization, deformation of vulcanization molding products, etc. are sometimes observable.

When a bisamidoxime compound is used as a vulcanizing agent on the other hand, good roll kneadability and press formability can be obtained without any poor flowing, rough vulcanization molding product surfaces, deformation of vulcanization molding products, etc. Physical properties are no no less than those obtained when the bisamidrazone compound.

What is claimed is:

1. A bisamidoxime compound represented by the following general formula:

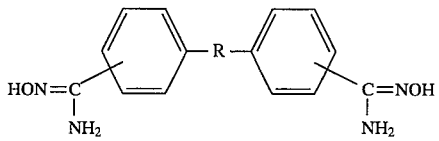

where R is an alkylidene group having 1 to 6 carbon atoms, or a perfluoroalkylidene group having 1 to 10 carbon atoms.

2. A bisamidoxime compound represented by the following general formula:

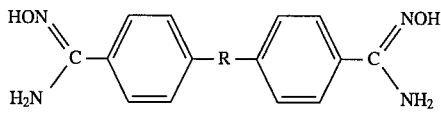

where R is an alkylidene group having 1 to 6 carbon atoms, or a perfluoroalkylidene group having 1 to 10 carbon atoms.

3. A bisamidoxime compound represented by the following formula:

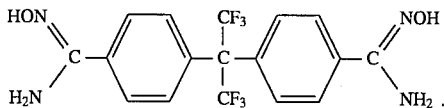

4. A bisamidoxime compound represented by the following formula:

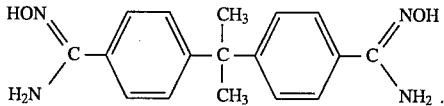

5. A process for preparing a bisamidoxime compound represented by the following general formula:

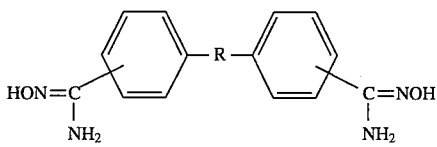

where R is an alkylidene group having 1 to 6 carbon atoms, or a perfluoroalkylidene group having 1 to 10 carbon atoms, which comprises reacting a bis(cyanophenyl) compound represented by the following general formula:

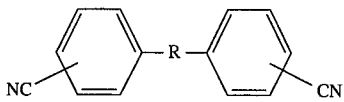

where R has the same meanings as defined above, with hydroxylamine or its salt.

6. A fluorine-containing elastomer composition, which comprises a fluorine-containing elastomer having cyano groups as cross-linkable groups and a bisamidoxime compound represented by the following general formula:

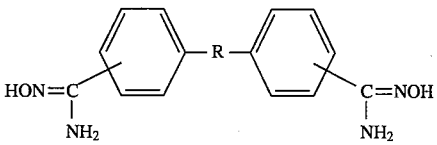

where R is an alkylidene group having 1 to 6 carbon atoms, or a perfluoroalkylidene group having 1 to 10 carbon atoms, as a vulcanizing agent.

7. A fluorine-containing elastomer composition according to claim 6, wherein a fluorine-containing elastomer is a terpolymer consisting of 45 to 75% by mole of tetrafluoroethylene, 54.8 to 20% by mole of perfluoro(lower alkyl vinyl ether) and 0.2 to 5% by mole of perfluoro unsaturated nitrile compound.

8. A fluorine-containing elastomer composition according to claim 6, wherein about 0.2 to about 5 parts by weight of the bisamidoxime compound is used per 100 parts by weight of the fluorine-containing elastomer having cyano groups as cross-linkable groups.

* * * * *